United States Patent
Johns et al.

(10) Patent No.: US 12,178,936 B2
(45) Date of Patent: Dec. 31, 2024

(54) MEDICAL IMPLANTS AND METHODS OF MANUFACTURE

(71) Applicant: DiFusion, Inc., Austin, TX (US)

(72) Inventors: Derrick Johns, Liberty Hill, TX (US); Joseph J. Crudden, Hudson, NH (US); Sriram Sankar, Austin, TX (US)

(73) Assignee: DiFusion, Inc., Austin, TX (US)

( * ) Notice: Subject to any disclaimer, the term of this patent is extended or adjusted under 35 U.S.C. 154(b) by 0 days.

(21) Appl. No.: 18/373,603

(22) Filed: Sep. 27, 2023

(65) Prior Publication Data

US 2024/0016975 A1    Jan. 18, 2024

Related U.S. Application Data

(62) Division of application No. 17/361,582, filed on Jun. 29, 2021, now abandoned.
(Continued)

(51) Int. Cl.
*A61K 33/00* (2006.01)
*A61K 33/06* (2006.01)
(Continued)

(52) U.S. Cl.
CPC ............ *A61L 27/025* (2013.01); *A61K 33/00* (2013.01); *A61K 33/06* (2013.01); *A61K 33/30* (2013.01); *A61K 33/34* (2013.01); *A61K 33/38* (2013.01); *A61L 27/08* (2013.01); *A61L 27/18* (2013.01); *A61L 2300/102* (2013.01);
(Continued)

(58) Field of Classification Search
CPC ........ A61L 27/025; A61L 27/08; A61L 27/18; A61L 2300/102; A61L 2300/104; A61L 2300/404; A61L 2430/10; A61L 2400/18; A61L 27/446; A61L 27/54; A61K 33/00; A61K 33/06; A61K 33/30; A61K 33/34; A61K 33/38; A61K 6/20; A61K 6/58; A61K 6/69; A61K 6/844; A61K 6/869;
(Continued)

(56) References Cited

U.S. PATENT DOCUMENTS

| 4,088,737 A | 5/1978 | Thomas et al. |
| 4,596,574 A | 6/1986 | Urist |

(Continued)

FOREIGN PATENT DOCUMENTS

| BY | 11260 C1 | 10/2008 |
| CA | 2171703 A1 | 4/1995 |

(Continued)

OTHER PUBLICATIONS

International Search Report and Written Opinion mailed Nov. 16, 2023 in corresponding PCT application No. PCT/US2023/026337.
(Continued)

*Primary Examiner* — Ernst V Arnold
(74) *Attorney, Agent, or Firm* — NIELDS, LEMACK & FRAME, LLC

(57) ABSTRACT

Anti-biofilm osseointegrating and/or tissue-integrating implantable biomaterial devices that optionally can elute therapeutic ions such as magnesium, silver, copper and/or zinc. In certain embodiments, the devices are engineered to produce structures suitable as implants having a relatively high surface population of zeolite. Methods of producing the devices are also disclosed.

6 Claims, 1 Drawing Sheet

Related U.S. Application Data

(60) Provisional application No. 63/046,191, filed on Jun. 30, 2020.

(51) Int. Cl.
| | |
|---|---|
| *A61K 33/30* | (2006.01) |
| *A61K 33/34* | (2006.01) |
| *A61K 33/38* | (2006.01) |
| *A61L 27/02* | (2006.01) |
| *A61L 27/08* | (2006.01) |
| *A61L 27/10* | (2006.01) |
| *A61L 27/18* | (2006.01) |
| *A61L 27/30* | (2006.01) |

(52) U.S. Cl.
CPC ... *A61L 2300/104* (2013.01); *A61L 2300/404* (2013.01); *A61L 2430/10* (2013.01)

(58) Field of Classification Search
CPC . B29C 33/56; B29C 45/0001; B29C 45/1701; B29C 2045/0079; A61C 8/0012
See application file for complete search history.

(56) References Cited

U.S. PATENT DOCUMENTS

| | | | |
|---|---|---|---|
| 4,612,337 A | 9/1986 | Fox et al. |
| 4,615,705 A | 10/1986 | Scales et al. |
| 4,775,585 A | 10/1988 | Hagiwara et al. |
| 4,775,586 A | 10/1988 | Bohrn et al. |
| 4,778,469 A | 10/1988 | Lin |
| 4,861,808 A | 8/1989 | Billington et al. |
| 4,906,464 A | 3/1990 | Yamamoto et al. |
| 4,911,898 A | 3/1990 | Hagiwara et al. |
| 4,911,899 A | 3/1990 | Hagiwara et al. |
| 4,923,450 A | 5/1990 | Maeda et al. |
| 4,938,955 A | 7/1990 | Niira et al. |
| 4,938,958 A | 7/1990 | Niira et al. |
| 4,957,817 A | 9/1990 | Chau et al. |
| 4,959,268 A | 9/1990 | Hagiwara et al. |
| 5,003,638 A | 4/1991 | Miyake et al. |
| 5,100,671 A | 3/1992 | Maeda et al. |
| 5,151,122 A | 9/1992 | Atsumi et al. |
| 5,180,585 A | 1/1993 | Jacobson et al. |
| 5,192,590 A | 3/1993 | Sherman |
| 5,256,390 A | 10/1993 | Hu |
| 5,266,534 A | 11/1993 | Atsumi et al. |
| 5,288,834 A | 2/1994 | Roovers et al. |
| 5,294,634 A | 3/1994 | Yamaguchi |
| 5,296,238 A | 3/1994 | Sugiura et al. |
| 5,374,335 A | 12/1994 | Lindgren et al. |
| 5,443,513 A | 8/1995 | Moumene et al. |
| 5,474,797 A | 12/1995 | Sioshansi et al. |
| 5,478,563 A | 12/1995 | Erami et al. |
| 5,492,763 A | 2/1996 | Barry et al. |
| 5,522,904 A | 6/1996 | Moran et al. |
| 5,556,699 A | 9/1996 | Niira et al. |
| 5,595,750 A | 1/1997 | Jacobson et al. |
| 5,604,007 A | 2/1997 | Shore |
| 5,607,464 A | 3/1997 | Trescony et al. |
| 5,609,629 A | 3/1997 | Fearnot et al. |
| 5,614,568 A | 3/1997 | Mawatari et al. |
| 5,646,077 A | 7/1997 | Matsunaga et al. |
| 5,647,858 A | 7/1997 | Davidson et al. |
| 5,688,561 A | 11/1997 | Ichikawa et al. |
| 5,709,870 A | 1/1998 | Yoshimura et al. |
| 5,731,087 A | 3/1998 | Fan et al. |
| 5,753,251 A | 5/1998 | Burrell et al. |
| 5,756,145 A | 5/1998 | Darouiche |
| 5,770,255 A | 6/1998 | Burrell et al. |
| 5,783,570 A | 7/1998 | Yokota et al. |
| 5,871,537 A | 2/1999 | Holman et al. |
| 5,948,019 A | 9/1999 | Shu et al. |
| 6,015,816 A | 1/2000 | Kostyniak et al. |
| 6,090,732 A | 7/2000 | Ito et al. |
| 6,180,606 B1 | 1/2001 | Chen et al. |
| 6,248,342 B1 | 6/2001 | Trogolo et al. |
| 6,267,590 B1 | 7/2001 | Barry et al. |
| 6,296,863 B1 | 10/2001 | Trogolo et al. |
| 6,436,422 B1 | 8/2002 | Trogolo et al. |
| 6,471,993 B1 | 10/2002 | Shastri et al. |
| 6,582,715 B1 * | 6/2003 | Barry .................. A61L 27/04 |
| | | | 623/23.57 |
| 6,585,767 B1 | 7/2003 | Holley et al. |
| 6,720,006 B2 | 4/2004 | Hanke et al. |
| 6,723,428 B1 | 4/2004 | Foss et al. |
| 6,866,859 B2 | 3/2005 | Trogolo et al. |
| 6,946,196 B2 | 9/2005 | Foss |
| 6,984,392 B2 | 1/2006 | Bechert et al. |
| 6,994,883 B2 | 2/2006 | Layrolle et al. |
| 7,150,884 B1 | 12/2006 | Hilgren et al. |
| 7,270,813 B2 | 9/2007 | Shimp et al. |
| 7,354,605 B2 | 4/2008 | Trogolo et al. |
| 7,357,949 B2 | 4/2008 | Trogolo et al. |
| 8,652,645 B2 | 2/2014 | Dingeldein et al. |
| 8,821,912 B2 | 9/2014 | Crudden et al. |
| 8,840,914 B2 | 9/2014 | Crudden et al. |
| 9,107,765 B2 * | 8/2015 | Ghiselli ................ A61F 2/28 |
| 9,132,576 B2 | 9/2015 | Crudden et al. |
| 9,375,321 B2 | 6/2016 | Whang et al. |
| 9,492,584 B2 | 11/2016 | Crudden et al. |
| 2002/0099449 A1 | 7/2002 | Speitling |
| 2003/0031687 A1 | 2/2003 | Falder et al. |
| 2004/0109937 A1 | 6/2004 | Jennissen et al. |
| 2005/0058682 A1 | 3/2005 | Sharratt |
| 2005/0064176 A1 | 3/2005 | Terry |
| 2005/0149196 A1 | 7/2005 | Zucherman et al. |
| 2005/0170070 A1 | 8/2005 | Layrolle et al. |
| 2005/0203529 A1 | 9/2005 | Boehm et al. |
| 2006/0052479 A1 | 3/2006 | Cougoulic |
| 2006/0069438 A1 | 3/2006 | Zucherman et al. |
| 2006/0161256 A1 | 7/2006 | Ziegler et al. |
| 2006/0177379 A1 | 8/2006 | Asgari |
| 2006/0259020 A1 | 11/2006 | Sharratt |
| 2006/0265065 A1 | 11/2006 | Bagga et al. |
| 2006/0280803 A1 | 12/2006 | Kumar et al. |
| 2007/0015110 A1 | 1/2007 | Zhang et al. |
| 2007/0031515 A1 | 2/2007 | Stucky et al. |
| 2007/0110825 A1 | 5/2007 | Taniguchi et al. |
| 2007/0267029 A1 | 11/2007 | Mason |
| 2007/0276337 A1 | 11/2007 | Trieu |
| 2007/0299472 A1 | 12/2007 | Brighton |
| 2008/0032119 A1 | 2/2008 | Feldhahn et al. |
| 2008/0033572 A1 | 2/2008 | D'Antonio et al. |
| 2008/0063671 A1 | 3/2008 | Morris et al. |
| 2008/0208340 A1 | 8/2008 | Boyd et al. |
| 2008/0249637 A1 | 10/2008 | Asgari |
| 2008/0258337 A1 | 10/2008 | Ajbani et al. |
| 2008/0268011 A1 | 10/2008 | Goldmann et al. |
| 2008/0286329 A1 | 11/2008 | Campbell et al. |
| 2009/0012612 A1 | 1/2009 | White et al. |
| 2009/0134542 A1 | 5/2009 | Eisenhut et al. |
| 2009/0238850 A1 | 9/2009 | Greener |
| 2010/0010632 A1 | 1/2010 | Bourges et al. |
| 2010/0082072 A1 | 4/2010 | Sybert et al. |
| 2010/0099058 A1 | 4/2010 | Wang |
| 2010/0114317 A1 | 5/2010 | Lambrecht et al. |
| 2010/0204699 A1 | 8/2010 | Wei et al. |
| 2010/0204802 A1 | 8/2010 | Wilson et al. |
| 2010/0215643 A1 | 8/2010 | Clevenger et al. |
| 2011/0022181 A1 | 1/2011 | Kasahara et al. |
| 2012/0064139 A1 | 3/2012 | McGrath |
| 2012/0141599 A1 | 6/2012 | Johns et al. |
| 2012/0292807 A1 | 11/2012 | Hulliger et al. |
| 2012/0315340 A1 | 12/2012 | Crudden et al. |
| 2012/0323339 A1 | 12/2012 | Graells et al. |
| 2013/0004585 A1 | 1/2013 | Crudden et al. |
| 2013/0037991 A1 | 2/2013 | Crudden et al. |
| 2013/0073042 A1 | 3/2013 | Ghiselli et al. |
| 2014/0170238 A1 | 6/2014 | Cliff et al. |
| 2014/0366362 A1 | 12/2014 | Crudden et al. |
| 2015/0342747 A1 | 12/2015 | Whang et al. |
| 2016/0256607 A1 | 9/2016 | Francis et al. |
| 2016/0296322 A1 | 10/2016 | Edelman et al. |

(56) References Cited

U.S. PATENT DOCUMENTS

| | | |
|---|---|---|
| 2017/0021061 A1 | 1/2017 | Crudden et al. |
| 2019/0298523 A1 | 10/2019 | Crudden et al. |
| 2019/0298886 A1 | 10/2019 | Crudden et al. |
| 2019/0365954 A1 | 12/2019 | Turng et al. |
| 2020/0315802 A1 | 10/2020 | Crudden et al. |
| 2020/0338237 A1 | 10/2020 | Crudden et al. |
| 2020/0338238 A1 | 10/2020 | Crudden et al. |
| 2021/0402052 A1 | 12/2021 | Johns et al. |

FOREIGN PATENT DOCUMENTS

| | | |
|---|---|---|
| CN | 1732025 A | 2/2006 |
| CN | 100360193 C | 1/2008 |
| CN | 101234304 A | 8/2008 |
| CN | 101238166 A | 8/2008 |
| DE | 3228849 A1 | 2/1984 |
| DE | 10055465 A1 | 5/2002 |
| EA | 011594 B1 | 4/2009 |
| EP | 0116865 A1 | 8/1984 |
| EP | 0224856 A2 | 6/1987 |
| EP | 0253663 A2 | 1/1988 |
| EP | 0722660 A2 | 7/1996 |
| EP | 1813292 A1 | 8/2007 |
| FR | 2848856 A1 | 6/2004 |
| FR | 2912740 A1 | 8/2008 |
| FR | 2915088 A1 | 10/2008 |
| JP | 2512324 B2 | 7/1996 |
| JP | 2003-513682 A | 4/2003 |
| JP | 2004-523302 A | 8/2004 |
| KR | 10-2009-0031668 A | 3/2009 |
| RU | 2107121 C1 | 3/1998 |
| RU | 2313370 C2 | 12/2007 |
| RU | 2338557 C2 | 11/2008 |
| WO | 84/01721 A1 | 5/1984 |
| WO | 99/07326 A2 | 2/1999 |
| WO | 00/30697 A1 | 6/2000 |
| WO | 00/32247 A2 | 6/2000 |
| WO | 00/64505 A1 | 11/2000 |
| WO | 03/086495 A1 | 10/2003 |
| WO | 2004/058319 A1 | 7/2004 |
| WO | 2006/069677 A2 | 7/2006 |
| WO | 2007/019461 A2 | 2/2007 |
| WO | 2008/037751 A2 | 4/2008 |
| WO | 2008/039488 A2 | 4/2008 |
| WO | 2008/128342 A1 | 10/2008 |
| WO | 2008/150867 A2 | 12/2008 |
| WO | 2009/099559 A2 | 8/2009 |
| WO | 2010/114827 A1 | 10/2010 |
| WO | 2011/156540 A2 | 12/2011 |
| WO | 2014/152649 A1 | 9/2014 |

OTHER PUBLICATIONS

International Search Report/Written Opinion mailed May 13, 2010 in co-pending PCT application No. PCT/US10/29180.
International Preliminary Report on Patentability dated Dec. 6, 2011 in co-pending PCT application No. PCT/US10/29180.
Chinese Communication issued Sep. 26, 2012 in co-pending Chinese patent application No. CN 201080015851.3.
European communication mailed Feb. 6, 2014 in co-pending European patent application No. 10759287.5.
Russian Communication, with English translation, issued Oct. 9, 2013 in co-pending Russian patent application No. RU 2011144020.
Russian communication dated Apr. 14, 2014 in co-pending Russian patent application No. 2011144020/15(066044).
European communication dated Oct. 7, 2015 in co-pending European patent application No. 15163787.3.
Korean communication, with English translation, dated Jan. 12, 2016 in co-pending Korean patent application No. 10-2011-7023593.
Indian communication dated Sep. 22, 2017 in co-pending Indian patent application No. 7793/DELNP/2011.
Brazilian communication, with English translation, dated Aug. 27, 2019 in co-pending Brazilian patent application No. PI1015155-9.
Brazilian communication, with English translation, dated Dec. 2, 2019 in co-pending Brazilian patent application No. PI1015155-9.
International Search Report and Written Opinion mailed Aug. 19, 2011 in co-pending PCT application No. PCT/US2010/058009.
International Preliminary Report on Patentability mailed Jun. 7, 2012 in co-pending PCT application No. PCT/US2010/058009.
Extended European Search Report mailed May 21, 2013 in co-pending European patent application No. EP 10833925.0.
Chinese Communication issued Dec. 3, 2013 in co-pending Chinese patent application No. CN 201080062338.X.
Chinese communication, with English translation, issued Jul. 1, 2014 in co-pending Chinese patent application No. 201080062338.X.
Chinese communication, with English translation, issued Sep. 30, 2014 in co-pending Chinese patent application No. 201080062338.X.
Russian communication, with English translation, dated Sep. 15, 2014 in co-pending Russian patent application No. 2012126078/15(040280).
Russian Communication, with English translation, issued Jan. 12, 2015 in co-pending Russian patent application 2012126078/15(040280).
Chinese communication, with English translation, dated Mar. 14, 2017 in co-pending Chinese patent application No. 201510165624.3.
Indian communication dated Sep. 27, 2017 in co-pending Indian patent application No. 4965/DELNP/2012.
Chinese communication, with English translation, dated Jan. 2, 2018 in co-pending Chinese patent application No. 201510165624.3.
Notice of opposition, dated Jan. 23, 2018 in co-pending European patent application No. 10833925.0.
Brazilian communication, with English translation, dated Apr. 17, 2018 in co-pending Brazilian patent application No. BR 11 2012 012603-2.
Brazilian communication, with English translation, dated Aug. 22, 2018 in co-pending Brazilian patent application No. BR 112012012603-2.
European communication dated Oct. 26, 2018 in co-pending European patent application No. 10833925.0.
International Search Report and Written Opinion mailed Aug. 25, 2011 in co-pending PCT application No. PCT/US2010/059868.
International Preliminary Report on Patentability mailed Jun. 21, 2012 in co-pending PCT application No. PCT/US2010/059868.
European Communication mailed Aug. 27, 2013 in co-pending European patent application No. EP 10836743.4.
European communication dated May 27, 2015 in co-pending European patent application No. 10836743.4.
English translation of Chinese Communication issued Oct. 30, 2013 in co-pending Chinese patent application No. CN 201080063584.7.
Chinese communication, with English translation, issued Jun. 17, 2014 in co-pending Chinese patent application No. CN 201080063584.7.
Russian Communication, with English translation, issued Nov. 20, 2013 in co-pending Russian patent application No. RU 2012129171.
Russian communication dated Apr. 17, 2014 in co-pending Russian patent application No. 2012129171/15(045686).
European communication dated Oct. 27, 2015 in co-pending European patent application No. 10836743.4.
Indian communication dated Sep. 12, 2017 in co-pending Indian patent application No. 5255/DELNP/2012.
Brazilian communication, with English translation, dated Jun. 30, 2018 in co-pending Brazilian patent application No. BR112012016027-3.
International Search Report and Written Opinion mailed Jan. 9, 2012 in co-pending PCT application No. PCT/US2011/035468.
International Preliminary Report on Patentability mailed Aug. 7, 2012 in co-pending PCT application No. PCT/US2011/035468.
European Communication mailed Sep. 4, 2013 in co-pending European patent application No. EP 11778401.7.

(56) References Cited

OTHER PUBLICATIONS

Canadian communication dated Apr. 9, 2014 in co-pending Canadian patent application No. 2,795,836.
Chinese Communication issued Jan. 6, 2014 in co-pending Chinese patent application No. CN 201180023035.1.
Chinese communication, with English translation, issued Jul. 7, 2014 in co-pending Chinese patent application No. CN 201180023035.1.
Chinese communication, with English translation, mailed Mar. 30, 2015 in co-pending Chinese patent application No. 201180023035.1.
Mexican communication, with English translation, dated Apr. 17, 2015 in co-pending Mexican patent application No. MX/a/2012/012710.
Russian communication, with English translation, dated Jun. 3, 2015 in co-pending Russian patent application No. 2012152640.
Chinese communication, with English translation, dated Oct. 10, 2015 in co-pending Chinese patent application No. 201180023035.1.
Russian communication, with English Translation, dated Dec. 28, 2015 in co-pending Russian patent application No. 2012152640.
Russian communication, with English translation, dated Jan. 25, 2017 in co-pending Russian patent application No. 2012152640.
Chinese communication, with English translation, dated Mar. 2, 2017 in co-pending Chinese patent application No. 201180023035.1.
Office action mailed Oct. 25, 2017 in co-pending U.S. Appl. No. 15/287,845.
Final rejection mailed Apr. 6, 2018 in co-pending U.S. Appl. No. 15/287,845.
Office action mailed Aug. 24, 2018 in co-pending U.S. Appl. No. 15/287,845.
Final rejection mailed Mar. 4, 2019 in co-pending U.S. Appl. No. 15/287,845.
Office action mailed Sep. 16, 2019 in co-pending U.S. Appl. No. 15/287,845.
Final rejection mailed Jan. 28, 2020 in co-pending U.S. Appl. No. 15/287,845.
Office action mailed Sep. 29, 2020 in co-pending U.S. Appl. No. 15/287,845.
Final rejection mailed Mar. 9, 2021 in co-pending U.S. Appl. No. 15/287,845.
Office action mailed Jul. 9, 2021 in co-pending U.S. Appl. No. 15/287,845.
Office action mailed Aug. 3, 2021 in co-pending U.S. Appl. No. 16/923,486.
Office action mailed Aug. 3, 2021 in co-pending U.S. Appl. No. 16/923,495.
Office action mailed Sep. 2, 2020 in co-pending U.S. Appl. No. 16/369,141.
Office action mailed Jan. 5, 2021 in co-pending U.S. Appl. No. 16/369,141.
Final rejection mailed Jul. 16, 2021 in co-pending U.S. Appl. No. 16/369,141.
Office action mailed Sep. 2, 2020 in co-pending U.S. Appl. No. 16/369,147.
Office action mailed Jan. 5, 2021 in co-pending U.S. Appl. No. 16/369,147.
Final rejection mailed Jul. 19, 2021 in co-pending U.S. Appl. No. 16/369,147.
International Search Report and Written Opinion mailed Sep. 11, 2023 in corresponding PCT application No. PCT/US2023/018297.
Agarwal et al., Biomaterial strategies for engineering implants for enhanced osseointegration and bone repair. Adv Drug Deliv Rev. Nov. 1, 2015;94:53-62.
Becker et al., Covalent grafting of the RGD-peptide onto polyetheretherketone surfaces via Schiff base formation. ScientificWorldJournal. Oct. 21, 2013;2013:616535.
Dong et al., Towards near-permanent CoCrMo prosthesis surface by combining micro-texturing and low temperature plasma carburising. J Mech Behav Biomed Mater. Mar. 2015;55:215-227.
Jemat et al., Surface Modifications and Their Effects on Titanium Dental Implants. Biomed Res Int. 2015;2015:791725.
Poulsson et al., "Surface Modification Techniques of PEEK, Including Plasma Surface Treatment", Chapter 11, PEEK Biomaterials Handbook, pp. 179-201, Jan. 2019.
Office action mailed Dec. 22, 2021 in co-pending U.S. Appl. No. 16/905,110.
Office action mailed Aug. 31, 2022 in co-pending U.S. Appl. No. 17/361,582.
Office action mailed Sep. 21, 2022 in co-pending U.S. Appl. No. 17/361,582.
Final Rejection mailed Jan. 6, 2023 in co-pending U.S. Appl. No. 17/361,582.
Office action mailed Jul. 6, 2023 in co-pending U.S. Appl. No. 17/361,582.
Final Rejection mailed Aug. 24, 2023 in co-pending U.S. Appl. No. 17/361,582.
European communication dated Mar. 3, 2017 in co-pending European patent application No. 11778401.7.
Russian communication, with English translation, dated Nov. 15, 2017 in co-pending Russian patent application No. 2012152640.
Brazilian communication, with English translation, dated Apr. 3, 2018 in co-pending Brazilian patent application No. BR 11 2012 026636-5.
Brazilian communication, with English translation, dated Jul. 26, 2018 in co-pending Brazilian patent application No. BR 112012026636-5.
Indian communication dated Jun. 25, 2019 in co-pending Indian patent application No. 10427/DELNP/2012.
International Search Report and Written Opinion mailed Jul. 21, 2014 in co-pending PCT application No. PCT/US14/27576.
International Preliminary Report on Patentability mailed Apr. 8, 2015 in co-pending PCT application No. PCT/US14/27576.
Additive Manufacturing, AM Basics, pp. 1-3, 2021.
Antimicrobial Agents and Chemotherapy, Dec. 2005, vol. 49, No. 12, p. 4853-4859, "Role of Silver Ions in Destabilization of Intermolecular Adhesion Forces Measured by Atomic Force Microscopy in Staphylococcus epidermidis Biofilms", Chaw, et al.
Journal of the Brazilian Chemical Society, vol. 19,. No. 1, Sao Paolo, 2008, pp. 1-11, downloaded from the interenet Mar. 1, 2013, "Preparation and characterization of poly(ether ether ketone) derivatives", Conceicao, et al.
Cowan et al., "Antimicrobial Efficacy of a Silver-Zeolite Matrix Coating on Stainless Steel", Journal of Industrial Microbiology and Biotechnology, vol. 30, pp. 102-106, 2003.
DiFusion Technologies research paper, created Oct. 14, 2013, "Novel Orthopedic Implant Material Protects Osteoblast Viability in the Presence of Biofilm-Forming MRSA", 4 pages.
Emerging Infectious Diseases, vol. 7, No. 2, Mar.-Apr. 2001, pp. 277-281, "Biofilms and Device-Associated Infections", Donlan.
Clinical Microbiology Reviews, Apr. 2002, vol. 15, No. 2, pp. 155-166, Focus, "Bacterial Adhesion: Seen Any Good Biofilms Lately?", Dunne, Jr., et al.
"Antimicrobial Efficacy of a novel Orthobiologic PEEK in treating Surgical Site Spine Infections", http://www. difusiontech.com/wp-content/uploads/NASS-Summer-Conference_2013-Abstract_final2.pdf, NASS Summer Session, Aug. 2-5, 2013, Naples, FL, 2 pages, Eastlack, et al.
"Exploring the efficacy of a self-sterilizing orthobiologic PEEK as a viable biomaterial for spinal surgery", http://www.nassannualmeeting.org/Documents/AMB_FinalProgram.pdf, Abstract, NASS Annual Meeting, Oct. 9-12, 2013 NewOrleans, LA, 3 pages, Eastlack, et al.
EPA Synthetic Fibers reference, Organic Chemical Process Industry, www.epa.gov/sites/production/files/2020-10/documents/c06s09_0.pdf, 1995.
Gao et al., "Cooling Rate Influences in Carbon Fibre/PEEK Composites. Part 1. Crystallinity and Interface Adhesion", Composites Part A, vol. 31, pp. 517-530, 2000.

(56) References Cited

OTHER PUBLICATIONS

The Journal of Biological Chemistry, vol. 263, No. 13, May 5, 1988, pp. 6276-6280, "Regulation of the Enterotoxin B Gene in *Staphylococcus aureus*", Gaskill, et al.
Gun Nozzles for Every Application, Gema Switzerland GmbH, pp. 1-23, 2015.
Neurosurg. Focus, vol. 10, No. 4, 2001, 7 pages, "Bone Graft Substitutes for the Promotion of Spinal Arthrodesis", Helm, et al.
Journal of the Physical Society of Japan, vol. 77, No. 6, Jun. 2008, 064712, "Photoluminescence of the Dehydrated Ag-type Zeolite A Packed under Air", pp. 064712-1-064712-7, Hoshino, et al.
Ann Nutr Metab., 1993, 37(5):245-252, 2 page abstract, "Impaired mechanical strength of bone in experimental copper deficiency", Jonas, et al.
European Cells and Materials, vol. 8, 2004, pp. 37-57, "Concise Review of Mechanisms of Bacterial Adhesion to Biomaterials and of Techniques Used in Estimating Bacteria-Material Interactions", Katsikogianni, et al.
J Bone Miner Res., Nov. 1992, vol. 7(11), pp. 1281-1289, 1 page Abstract, http://www.ncbi.nlm.nih.gov/pubmed/1334616, "Zeolite A increases proliferation, differentiation, and transforming growth factor beta production in normal adult human osteoblast-like cells in vitro", Keeting, et al.
Medical Design Technology Online, Jan. 28, 2010, 5 pages, http://www.mdtmag.com/scripts/ShowPR.asp?PUBCODE=046&ACCT=0006305&ISSUE . . . , "Taking a PEEK at Material Options for Orthopedics", Kinbrum.
National Institute of Standards and Technology (NIST) recommended practice guide, Special Publication 960-17, Sep. 2006, "Porosity and Specific Surface Area Measurements for Solid Materials", 91 pages, Klobes, et al.
Clin. Orthop. Relat. Res., Nov.-Dec. 1981, vol. 161, pp. 154-162, 1 page Abstract, "Antibacterial and osteoinductive properties of demineralized bone matrix treated with silver", Kramer, et al.
Medicaldevice-network.com, Jul. 2011, http://www.medicaldevice-network.com/features/feature128303, "PEEK performance: a next-generation biomaterial", 5 pages, Kurtz.
Biomaterials, vol. 28, 2007, pp. 4845-4869, "PEEK biomaterials in trauma, orthopedic, and spinal implants", Kurtz, et al.
Kwakye-Awuah et al., "Antimicrobial Action and Efficiency of Silver-Loaded Zeolite X", Journal of Applied Microbiology, vol. 104, pp. 1516-1524, 2008.
The Journal of Nutrition, 2002, http://jn.nutrition.org/content/132/10/3135.full.pdf+html, Nutrient Requirements, "Bone Morphology, Strength and Density Are Compromised in Iron-Deficient Rats and Exacerbated by Calcium Restriction", pp. 3135-3141, Medeiros, et al.
Micronized in the Pharmaceutical Industry, Collins Dictionary, 2021.
Journal of Polymer Science: Part B: Polymer Physics, 2004, vol. 42, pp. 1548-1563, "Poly(ether ether ketone)/Poly (aryl ether sulfone) Blends: Melt Rheological Behavior", Nandan, et al.
Net Motion, Inc., copyright 2003, http://www.netmotion.com/htm_files/wh_properties.htm#chem, pp. 1-8, downloaded from internet Mar. 1, 2013, All you want to know about Polyetheretherketone (PEEK), Chemical Resistance of PEEK, PEEK and Polymer chemical resistance.
Zinc Toxicity in Humans, 2007, Elsevier B.V. publication, pp. 1-7, Jerome Nriagu, School of Public Health, University of Michigan.
29th Edition of the Kunststoff Taschenbuch, 2004, pp. 514-517, Oberbach, et al.
BMC Musculoskeletal Disorders, 2013, 14:187, http://www.biomedcentral.com/1471-2474/14/187, 11 pages, "*Staphylococcus aureus* biofilms decrease osteoblast viability, inhibits osteogenic differentiation, and increases bone resorption in vitro", Sanchez, Jr., et al.
J. Phys. Chem. A, 2000, vol. 104, pp. 7473-7483, "Colors of Ag+-Exchanged Zeolite A.", Seifert, et al.
Rothman-Simeone-The Spine, 6th Edition, vol. II, Chapter 98, Garfin,, S., ed., "Postoperative Spinal Infections", 53 pages, Smith, et al.
United States Environmental Protection Agency, Silver-Copper Zeolite Data Review, Feb. 15, 1994, 3 pages.
VICI AG International, 2013, VICI JOUR—Technical Support, Chemical Resistance of PEEK and Other Polymers, Chart displaying PEEK and Polymer Chemical Resistance, 3 pages.
Wan et al., "Surface Modification of Medical Metals by Ion Implantation of Silver and Copper", Vacuum, vol. 81, pp. 1114-1118, 2007.
The Structure and Synthesis of Zeolite Molecular Sieves, Jilin University Press, Aug. 1987, 1st Edition, pp. 6 and 8, 4 pages, Xu, et al.
"Opisanie tseolita i ego svoysty", Aug. 4, 2004, https://web.archive.org/web/20040804124452/http://www.ceolit.smila.com/op.htm 04.08.2004, 3 pages.
Office Action—Restriction—mailed Jan. 23, 2014 in co-pending U.S. Appl. No. 13/260,571.
Office Action mailed May 12, 2014 in co-pending U.S. Appl. No. 13/260,571.
Final rejection mailed Oct. 16, 2014 in co-pending U.S. Appl. No. 13/260,571.
Office action mailed Apr. 22, 2015 in co-pending U.S. Appl. No. 13/260,571.
Final rejection mailed Nov. 17, 2015 in co-pending U.S. Appl. No. 13/260,571.
International Preliminary Report on Patentability issued Oct. 24, 2024 in co-pending PCT application No. PCT/US2023/018297.

\* cited by examiner

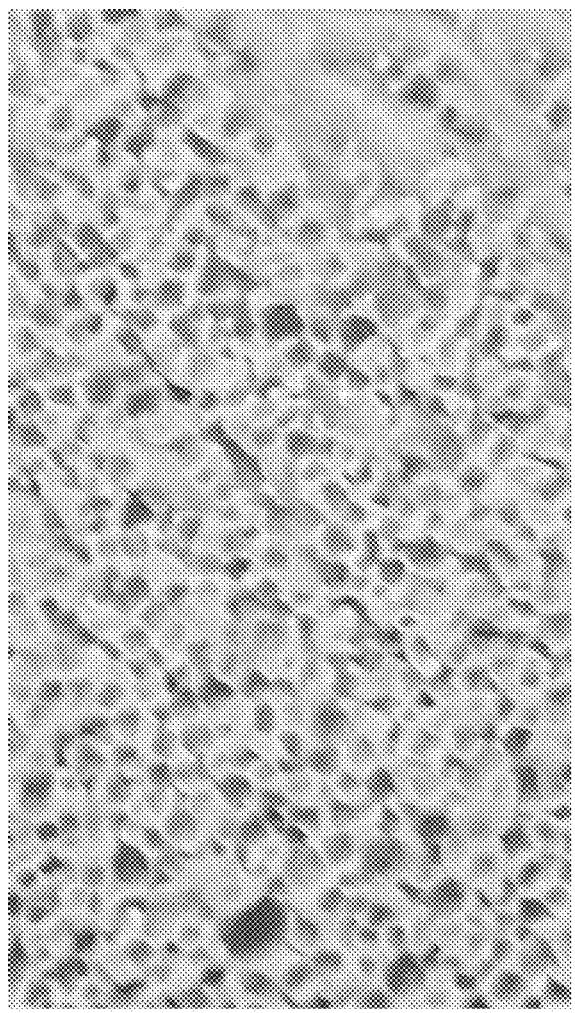

MEDICAL IMPLANTS AND METHODS OF MANUFACTURE

This application is a divisional of U.S. patent application Ser. No. 17/361,582 filed Jun. 29, 2021, which claims priority from U.S. Provisional Application Ser. No. 63/046,191 filed Jun. 30, 2020, the disclosures of which are hereby incorporated by reference.

BACKGROUND

Implantable biomaterials may be surgically implanted into the body for various reasons, including orthopedic applications (e.g., hip replacement, skull flaps, dental implants, spinal procedures, knee replacement, bone fracture repair, etc.), surgical repair applications (e.g., ACL screws, surgical meshes, etc.). In view of the structural integrity required by many such devices, particularly those involving bone repair or replacement, materials of fabrication are limited and generally consist of metal, plastic and composites.

The benefits derived from these devices are often offset by infection which in some cases can lead to sepsis and death. The most common organisms causing infections are *Staphylococcus epidermidis* and *Staphylococcus aureus*. *Staphylococcus epidermidis* is a major component of the normal bacterial flora of human skin and mucous membranes. It is a common pathogen that often colonizes patients in hospital settings who have surgical implants due to the microbes' ability to adhere to medical devices and form a biofilm. Additionally, methicillin-resistant *Staphylococcus aureus* (MRSA) is a type of *staphylococcus* bacteria that is resistant to many antibiotics is therefore of particular concern. Other gram-positive bacteria, gram-negative bacteria and fungal organisms also are causative organisms that may be problematic.

As microorganisms come in close proximity to the surface of the medical device, they will either be attracted or repelled by it depending on the sum of the different non-specific interactions. In biological systems, hydrophobic/hydrophilic interactions play an important role in the pathogenesis of a wide range of microbial infections.

The role of the neutralization of infectious agents, and the host response to foreign materials such as surgical meshes, orthopedic implants, and other devices, in normal tissue/organ development and tissue regeneration is important. Immune cells such as neutrophils, macrophages, and lymphocytes possess robust plasticity with respect to phenotype. For example, macrophages typically show a marked pro-inflammatory (M1-like) phenotype when presented with certain antigens (e.g., synthetic foreign materials or bacteria), but then transition to pro-healing, anti-inflammatory and constructive phenotype (M2-like) when subsequently influenced by alternative signaling molecules.

A "normal" response to injury involves an initial pro-inflammatory cell response that must then switch to a pro-healing phenotype lest there be continuous, non-healing inflammation and tissue destruction. The phenotype of cells such as macrophages can be determined, at least in part, by the expression of certain markers that are detected by immunolabeling. Macrophage phenotype during the early response (i.e., 7-14 days) to an implanted foreign material is predictive of the downstream outcome. An early M1-like response was associated with chronic inflammation and fibrosis; whereas an early M2-like response was associated with minimal fibrosis and constructive and functional tissue remodeling.

It is therefore important, if not critical, that implantable biomaterials be developed that promote activation of several genes associated with an M2-like macrophage phenotype. A desirable M1/M2 macrophage phenotype balance, and in particular, the early preferential polarization towards an M2 phenotype after implantation, can lead to a shorter pro-inflammatory period and earlier reparative process, which can be critical for effective osseointegration and/or tissue integration and ultimately implant success.

Certain polymeric materials, such as polyetherketoneketone (PEKK) and polyetheretherketone (PEEK) have been found to be a useful material for medical implants, particularly due to their modulus of elasticity which closely matches that of bone. However, in addition to strength characteristics, a suitable polymeric material for implant applications should interact well with tissue, and should osseointegrate with bone. The polymer should also be recognized by the host as natural so as to minimize or avoid becoming encapsulated by a fibrous apposition layer of soft tissue rather than becoming bonded or fused to bone and tissue cells.

However, many resins including PEEK are hydrophobic materials and bacteria tend to adhere easily to these types of surfaces. They are also organic materials which do not carry significant surface charges. Consequently, it would be desirable to develop a medical implant composed of one or more thermoplastic resins that has reduced hydrophobic properties, and/or that has a net negative charge, particularly at an exposed surface when implanted into a host.

The addition of ceramics such as zeolites to such resins helps accomplish this. In addition, zeolites can provide ion-exchange sites and can be loaded with antimicrobial metal ions that elute when in contact with the bodily fluid or tissue of a host, thereby imparting antimicrobial activity to the implant site. Since conventionally the zeolite has been uniformly distributed in the thermoplastic matrix, a composite with 10% loading, for example, will have 10% of the surface occupied by zeolite particles. While a higher concentration of zeolite at the surface is desirable, the amount of zeolite that can be loaded into a resin is limited in part by the desired or required biomechanical properties of the resulting composite implant. For example, an implant with more than about 12% uniformly distributed zeolite may not have the load-bearing characteristics necessary for load-bearing applications, such as spinal implantation.

It therefore would be beneficial to have a higher zeolite surface occupancy of the composite in order to enhance the therapeutic effects of the device, including osseointegration and tissue integration, without compromising the biomechanical and imaging properties of the device.

It therefore is an object of embodiments disclosed herein to provide methods for increasing the amount of zeolite at the surface of an implant, while maintaining the amount of zeolite, if any, in the main body of the implant, at a level that does not compromise the biomechanical properties of the implant.

It is a further object of embodiments disclosed herein to provide composite implants with an increased amount of zeolite at the surface of the implants.

SUMMARY

The shortcomings of the prior art have been overcome by embodiments disclosed herein, which relate to anti-biofilm osseointegrating and/or tissue-integrating implantable biomaterial devices that optionally can elute therapeutic ions such as magnesium, silver, copper and/or zinc. In certain embodiments, medical devices such as implants are engineered to produce structures suitable as implants having a relatively high surface population of zeolite. The resulting device may be formed into the shape of the desired implant, e.g., a hip stem; skull flap; spinal implant (e.g., an intervertebral spacer); dental implant; joint implant, e.g., a knee implant; screw, rod, hip stem; skull flap or trauma plate. In certain embodiments, the implants are orthopedic implants, such as spinal, knee and hip implants, and are so shaped or configured. In certain embodiments, the implant is an ACL screw such as an interference screw and is so shaped and configured.

In some embodiments, the biomaterial includes a polymer such as PEKK, PEEK, polylactic acid (PLA) and/or polymethyl (meth) acrylate.

In some embodiments, the biomaterial includes zeolite, and the zeolite optionally may be loaded with one or more therapeutic metal ions, such as magnesium, silver, copper and/or zinc, that exhibit antimicrobial properties when implanted into a body and exposed to bodily fluid or tissue. The devices, when implanted into a body and exposed to bodily fluid, may elute antimicrobial metal ions in a therapeutically effective amount. In certain embodiments, the source of antimicrobial activity includes ion-exchangeable cations contained in a zeolite. In certain embodiments, disclosed are methods of imparting antimicrobial activity to devices by controlling the delivery of certain cations through ion-exchange via a zeolite incorporated in the device introduced in a patient. Ceramics such as zeolite function as a cation cage, being able to be loaded with silver and other cations having antimicrobial properties. Metal zeolites can be used as an antimicrobial agent, such as by being mixed with the resins used as thermoplastic materials to make the implantable devices, or as coatings to be applied to the devices, or incorporated into the surface of the devices. The antimicrobial metal zeolites can be prepared by replacing all or part of the ion-exchangeable ions in zeolite with ammonium ions and antimicrobial metal ions. Such materials have been seen to perform extremely well in ovine and rabbit implant studies, showing high tissue compatibility, and bonding very well to bone and soft tissues alike.

In some embodiments, the zeolite does not contain an antimicrobial metal ion, yet imparts hydrophilicity and a negative charge to the implant. This helps prevent biofilm formation and enhances osseointegration and/or tissue integration. In embodiments where antimicrobial ions are present, the polymer/zeolite combination increases the ability of antimicrobial moieties to permeate in and kill bacterial pathogens in vivo.

In certain embodiments, the device is configured for use in spinal fusion (arthrodesis) which is often employed to stabilize an unstable spinal column due to structural deformity, trauma, degeneration, etc. Fusion is a surgical technique in which one or more vertebrae of the spine are united together ("fused") to reduce or eliminate relative motion between them or to fix the spatial relationship between them. Spinal fusions include posterolateral fusion, posterior lumbar interbody fusion, anterior lumbar interbody fusion, anterior/posterior spinal fusion, cervical fusion, thoracic fusion and interlaminar fusion. In certain embodiments, the devices are for insertion in an intervertebral space between adjacent vertebrae. In certain embodiments, a fusion site is identified between adjacent vertebrae and a bone graft is implanted at said site. In certain embodiments, the implant is a spinal interbody cage.

The hydrophilicity imparted by the zeolite results in an engineered biomaterial that interacts with the bone of a host and induces a bone/biomaterial fusion, or that interacts with the tissue of a host and induces tissue integration with the biomaterial. The presence of an enhanced amount of zeolite at the surface of the device results in a rapid transition from M1 proinflammatory macrophage phenotype to the M2 macrophage phenotype, thereby minimizing fibrous encapsulation and facilitating the deposition of site appropriate tissue ultimately yielding constructive and functional tissue ingrowth and remodeling. The negative charge imparted by the zeolite attracts and adheres the required precursor proteins for bone growth to the implant surface, and ultimately supports long term osseointegration.

In certain embodiments, zeolite particles are incorporated into the resin such that a negative charge is imparted to an exposed surface of the resin. The term "exposed surface" is intended to include one or more surfaces of an implantable device that when implanted into the body of a host, is exposed to or in contact with body tissue and/or bodily fluids of the host. The incorporation of zeolite to the exposed surface reduces the immune response, e.g., reduction of deleterious release of cytokines, such as interleukin 2, etc. upon implantation.

Accordingly, disclosed is a medical implant comprising a thermoplastic polymer defining a main body region and an exposed surface region, the exposed surface region being configured to be exposed to bodily fluid or tissue of a host when the medical implant is implanted in the host, the surface region comprising zeolite in an amount greater than 10% by weight. In some embodiments, the surface region comprises zeolite in an amount greater than 12% by weight. In some embodiments, the surface region comprises zeolite in an amount equal to or greater than 15% by weight. In some embodiments, the surface region comprises zeolite in an amount equal to or greater than 20% by weight. In some embodiments, the surface region comprises zeolite in an amount equal to or greater than 25% by weight. In some embodiments, the surface region comprises zeolite in an amount equal to or greater than 50% by weight. In some embodiments, the surface region comprises zeolite in an amount equal to or greater than 75% by weight. In some embodiments, the surface region comprises zeolite in an amount as high as 95% by weight. The resulting implant provides an excellent mechanical interlock with bone at the implant site.

Embodiments include exposed surface regions that have indentations or discontinuities, and are thus more porous than the main body region, and wherein a plurality of indentations in the surface region contain zeolite. In some embodiments, the main body region is devoid of zeolite. In other embodiments, the main body region contains between about 5 to about 12% zeolite.

In various embodiments, the medical implant may be configured as an ACL screw, such as an interference screw, a pedicle screw, a rod, a spinal implant such as an intervertebral spacer, a joint implant or replacement such as a knee implant, a hip stem, a skull flap, a dental implant or a trauma plate.

In certain embodiments, the thermoplastic polymer is PEEK. In some embodiments, the device includes carbon fibers to enhance mechanical strength. In some embodiments, the carbon fibers are in the main body region of the device. In some embodiments, the carbon fibers are in the surface region of the device. In some embodiments, the carbon fibers are in both the main body region and the surface region.

In various embodiments, a therapeutically effective amount of one or more antimicrobial and/or therapeutic metal ions may be added to the zeolite in the surface region to enable ion-exchange at the implant site to cause effective antimicrobial activity. In embodiments where the main body region includes zeolite, antimicrobial metal ions optionally may be added to the zeolite in the main body region. Suitable ions include silver, copper, zinc, mercury, tin, magnesium, lead, gold, bismuth, cadmium, chromium, strontium and thallium ions, calcium, silicon or combinations of one or more of the foregoing.

Various methods may be used to form the indentations in thee surface region of the article and incorporate the zeolite in the indentations formed, including creating the indentations with particles of a salt, creating the indentations with sandpaper or other substrate having indentation-forming members extending therefrom, and creating indentations with injection molding or press molding.

In a first exemplary embodiment, disclosed is a medical implant comprising a thermoplastic polymer defining a main body region and a surface region, said surface region being configured to be exposed to bodily fluid or tissue of a host when said medical implant is implanted in said host, said surface region comprising zeolite in an amount greater than 12% by weight.

In a first aspect of the first exemplary embodiment, the surface region contains a plurality of indentations containing said zeolite.

In a second aspect of the first exemplary embodiment, the surface region comprises zeolite in an amount greater than 15% by weight.

In a third aspect of the first exemplary embodiment, the surface region comprises zeolite in an amount greater than 20% by weight.

In a fourth aspect of the first exemplary embodiment, the surface region comprises zeolite in an amount greater than 25% by weight.

In a fifth aspect of the first exemplary embodiment, the surface region comprises zeolite in an amount greater than 30% by weight.

In a sixth aspect of the first exemplary embodiment, the surface region comprises zeolite in an amount greater than 50% by weight.

In a seventh aspect of the first exemplary embodiment, which may be based on any of the foregoing aspects, the main body region comprises zeolite in an amount of 12% by weight or less.

In an eighth aspect of the first exemplary embodiment, which may be based on any of the forgoing aspects, the implant is configured as an ACL screw.

In a ninth aspect of the first exemplary embodiment, which may be based on any of the first through seventh aspects, the implant is configured as a spinal implant, a knee implant, a hip stem, a skull flap, a dental implant or a trauma plate.

In a tenth aspect of the first exemplary embodiment, which may be based on any of the first through ninth aspects, the thermoplastic polymer comprises PEEK.

In an eleventh aspect of the first exemplary embodiment, which may be based on any of the first through tenth aspects, the medical implant further comprises carbon fibers.

In a twelfth aspect of the first exemplary embodiment, which may be based on any of the first through eleventh aspects, the zeolite comprises one or more antimicrobial and/or therapeutic metal ions.

In a thirteenth aspect of the first exemplary embodiment, which may be based on the twelfth aspect, the one or more metal ions is selected from the group consisting of silver, copper, zinc, magnesium and strontium.

In a second exemplary embodiment, disclosed is a method of making a medical implant having a main body region and an exposed surface region and comprising a polymer, the method comprising:
  a. heating the polymer to a molten state;
  b. contacting the polymer with a mixture of zeolite and indentation-forming agent with the application of force to form indentations in said exposed surface region and drive said mixture into the formed indentations of the exposed surface region;
  c. cooling the polymer; and
  d. washing the resulting composite.

In a first aspect of the second exemplary embodiment, the polymer is PEEK.

In a third exemplary embodiment, disclosed is a method of making a medical implant having a main body region and an exposed surface region and comprising a polymer, the method comprising:
  e. heating the polymer to a molten state;
  f. contacting the polymer with an indentation-forming member and zeolite to form indentations in said exposed surface region and drive the zeolite into the indentations in the exposed surface region; and
  g. cooling the resulting composite structure.

In a first aspect of the third exemplary embodiment, the polymer is PEEK.

In a second aspect of the third exemplary embodiment, the indentation-forming member comprises sandpaper.

In a third aspect of the second embodiment, which may be based on the second aspect of the third exemplary embodiment, the indentation-forming member comprises sandpaper.

In a fourth exemplary embodiment, disclosed is a method of making a medical implant having a main body region and an exposed surface region and comprising a polymer, the method comprising:
  h. injecting the polymer into the cavity of a mold at elevated temperature sufficient to melt the resin, the mold comprising a surface having a plurality of projections and a coating of zeolite;
  i. causing the melted polymer to contact said projections and driving the zeolite into the resin;
  j. removing the resulting article from the mold and cooling it.

BRIEF DESCRIPTION OF THE DRAWINGS

FIG. 1 is a photograph of a PEEK sample having increased surface area at the exposed surface region in accordance with certain embodiments.

DETAILED DESCRIPTION

A more complete understanding of the components, processes, systems and apparatuses disclosed herein can be obtained by reference to the accompanying drawings. The figures are merely schematic representations based on convenience and the ease of demonstrating the present disclosure, and are, therefore, not necessarily intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings. In the drawings and the following description below, it is to be understood that like numeric designations refer to components of like function.

The singular forms "a," "an," and "the" include plural referents unless the context clearly dictates otherwise.

As used in the specification, various devices and parts may be described as "comprising" other components. The terms "comprise(s)," "include(s)," "having," "has," "can," "contain(s)," and variants thereof, as used herein, are intended to be open-ended transitional phrases, terms, or words that do not preclude the possibility of additional components.

All ranges disclosed herein are inclusive of the recited endpoint and independently combinable (for example, the range of "from 2% to 10" is inclusive of the endpoints, 2% and 10%, and all the intermediate values).

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. The modifier "about" should also be considered as disclosing the range defined by the absolute values of the two endpoints. For example, the expression "from about 2 to about 4" also discloses the range "from 2 to 4."

It should be noted that many of the terms used herein are relative terms. For example, the terms "upper" and "lower" are relative to each other in location, i.e. an upper component is located at a higher elevation than a lower component, and should not be construed as requiring a particular orientation or location of the structure. As a further example, the terms "interior", "exterior", "inward", and "outward" are relative to a center, and should not be construed as requiring a particular orientation or location of the structure.

The terms "top" and "bottom" are relative to an absolute reference, i.e. the surface of the earth. Put another way, a top location is always located at a higher elevation than a bottom location, toward the surface of the earth.

Certain embodiments disclosed herein relate to a biomaterial formulated by incorporating a negatively charged zeolite into a base polymer, such as PEEK. The zeolite changes the surface topography, charging characteristics, and pH of the resulting composite in a predictable, suitable manner for the surgical environment and long-term healing of the host into whom the device is implanted. Attributes imparted by the zeolite include bone fusion, tissue fusion, biocompatibility, negative charge, hydrophilicity and osseoconductivity. Attributes provided by the PEEK base polymer include excellent imaging properties including radiolucency; biocompatibility, durability and versatility. The resulting combination provides a material construct having excellent workability and functionality.

Particularly compelling is the ability of the zeolite to mitigate or eliminate the immune response that is generated when naked PEEK (or other polymeric material) is implanted. It is a well-recognized problem that the human immune system reacts to the presence of naked PEEK as a foreign, unnatural substance, and as a damage/danger associated molecular pattern (DAMP). Consequently, the human body responds to the presence of naked PEEK by encapsulating it, causing bone resorption, and initiating a pain response. This is believed to be directly related to the hydrophobic, uncharged and water repellant nature of naked PEEK. Adding zeolite to the PEEK polymer increases proliferation, differentiation and transforms growth factor beta production in normal adult human osteoblast-like cells. The hydrophilic surface of the resulting implant downregulates pro-inflammatory cytokines interleukin 1 and 6, which modulates the immune response, facilitates the enhanced bone would healing and osseointegration, allows for early cell adhesion and ultimate osteoconduction, and reduces pain. IL1-Beta upregulates inflammatory immune-response, and IL6-Beta have been shown to have a direct relation to spinal disc pain. Both have been shown to down regulate osteoblast cells while up-regulating osteoclast cells, showing the increased fibrosis and resorption of bone with which naked hydrophobic PEEK has been well associated.

PEEK does not bond well to tissue and both PEEK and PEKK materials are susceptible to microbial contamination and to the support of bacterial biofilms. Composites of zeolite with PEEK produce a more hydrophilic and negatively charged surface which is less favorable to bacterial adhesion and more receptive to tissue attachment and integration. The hydrophilicity imparted by the zeolite results in an engineered biomaterial that interacts with the bone of the patient and induces a bone/biomaterial fusion. The presence of the zeolite also results in a rapid transition (e.g., faster than the transition that occurs in the absence of zeolite) from M1 proinflammatory macrophage phenotype to the M2 macrophage phenotype, thereby minimizing fibrous encapsulation and facilitating the deposition of site appropriate tissue ultimately yielding constructive and functional tissue remodeling. The negative charge imparted by the zeolite attracts and adheres the required precursor proteins for bone growth to the implant surface, and ultimately supports long term osseointegration.

The implant may comprise one or more of titanium, carbon fibers, biocompatible materials such as polyetheretherketone (PEEK), polyetherketoneketone (PEKK), polylactic acid, or other synthetic substances. Other suitable resins include low density polyethylene, polypropylene, ultra-high molecular weight polyethylene or polystyrene, polyvinyl chloride, ABS resins, silicones, rubber, polymethylmethacrylate (which melts at about 320° C.) and mixtures thereof, and reinforced resins, such as ceramic or carbon fiber-reinforced resins, particularly carbon fiber-reinforced PEEK. PEEK is particularly preferred, and melts at between 385 and 400 degrees Celsius.

In certain embodiments, zeolite particles may be incorporated into the polymer interbody cage to form a composite polymer resin/zeolite blend. In certain embodiments, the cage may be loaded with bioagents such as osseoconductive and/or osseoinductive agents to promote fusion. In some embodiments, the implant includes PEEK resin, and ceramic particles such as zeolite are uniformly incorporated into the main body region of the resin.

In order to increase the concentration of zeolite at the surface of the implant, zeolite may be forced into one or more surfaces of the implant. This may be applied to naked polymer (i.e., polymer with no zeolite incorporated into the main body region), or to a composite polymer resin/zeolite blend such as the composite prepared as above. Numerous methods may be used to accomplish the addition of zeolite to the exposed surface region of the implant article. For example, the polymer resin may be heated to a molten state, and the molten resin may be contacted with solid particles of an indentation forming agent or member, such as sodium chloride or sodium bicarbonate, with sufficient force to cause the particles to penetrate the resin surface and form indentations for occupation by zeolite. Suitable sodium chloride particles may have an average particle size ranging from 2 to 10 microns, as large as about 0.3-0.5 mm, or even larger. In some embodiments, the size of the indentation forming agent or member is similar to or about the same as the size of the zeolite particles. Other suitable indentation forming agents include potassium chloride, calcium phosphate, sulfate or silicate, sodium citrate, sodium tartrate, ammonium bicarbonate, ammonium chloride, sodium fluoride, potassium fluoride, sodium iodide, sodium nitrate, sodium sulphate, sodium iodate, and mixtures thereof. Residual exposed indentation forming agent can be washed from the surface of the implant using pure water. Preferably the salts are used in fine powder form and are water soluble so that they easily can be removed from the device such as after the device is cooled. Preferably the indentation forming agent is micronized salt, preferably sodium chloride, having an average particle size of about 0.3 mm. The depth of the penetration of the agent into the resin depends in part on the size of the solid particles. The resulting indentations creates a roughened surface area which can then be contacted with zeolite to load the zeolite into the indentations created by the agent. In some embodiments, the molten resin can be contacted with the zeolite and indentation forming agent simultaneously, such as by mixing the zeolite with the agent prior to contacting with the molten resin. Since the increased concentration of zeolite is only at the exposed surface of the article, the mechanical integrity of the article is not deleteriously compromised. As a result, zeolite amounts much greater than the typical about 12% maximum amount that can be tolerated in the case where zeolite is incorporated into the resin uniformly (from the stand point of maintaining acceptable mechanical integrity for purposes of implantation, particularly load-bearing implantation) can be added. Amounts ranging from about 15-95% zeolite at the surface of the implant article can be achieved. Preferred amounts include from 15-20 wt. % zeolite, 20-25 wt. % zeolite, 25-30 wt. % zeolite, 30-35 wt. zeolite, 35-40 wt. % zeolite, 45-50 wt. % zeolite, 50-55 wt. % zeolite, 55-60 wt. % zeolite, 60-65 wt. % zeolite, 65-70 wt. zeolite, 70-75 wt. % zeolite, 75-80 wt. % zeolite, 80-85 wt. zeolite, 85-90 wt. % zeolite, and 90-95 wt. % zeolite at the surface region of the article.

In some embodiments, the surface region is non-planar in view of the formed indentations, and the indentations have a depth of from about 4 to about 10 microns.

In another embodiment, the enhanced concentration of zeolite at the exposed surface region can be carried out by contacting the molten polymer with an indentation-forming member comprising a substrate having rigid protrusions or discontinuities extending therefrom. In the case of a flat or planar substrate, the angle of extension can be perpendicular to the axis defined by the planar substrate, or at an angle less than 90° to the axis defined by the planar substrate, such as 80°, 75°, 70°, 65°, 60° or less. The rigid protrusions can be integral to the substrate, or can be attached to the substrate by any suitable means such as with a suitable adhesive. They can be randomly oriented, or oriented in a uniform, equally spaced array. The protrusions can have various shapes, including spike-like or conical, cylindrical, pyramidal, etc. Preferably the rigid protrusions remain attached to the substrate and do not detach from the substrate and remain in the molten polymer.

One suitable indentation-forming member is sandpaper or any coated abrasive comprising a backing with abrasive grit attached thereto. Suitable abrasive grits include garnet, emery, aluminum oxide, silicon carbide, zirconium alumina, alumina and diamond. Suitable grit sizes are not particularly limited, and depend in part on the size of the indentations desired. Grit sizes ranging from about 40 to about 220 may be suitable, with grit sizes of 60 and 80 grit being preferred.

In some embodiments, the molten polymer may be contacted with the indentation-forming member coated with zeolite. For example, zeolite powder may be dusted or otherwise introduced onto the sandpaper or indentation-forming member substrate. Force may then be applied to assist or enhance the penetration of the rigid protrusions and zeolite into the molten resin. The force applied may be manual or automatic. Suitable amounts of force may include from about 10 to about 20 psi for about 30 seconds. This creates a roughened surface area which can then be contacted with zeolite to load the zeolite into the indentations in the exposed surface region created by the indentation-forming member. The process may be carried out multiple times with the same size grit size or with different size grits.

In yet a further embodiment, a molding operation can be used to form the implant and make one or more surfaces of the implant roughened or having an increased surface area due to formed indentations, such as injection molding. Thus, the mold itself may have a suitable profile such as one or more projections or discontinuities integral to it. Zeolite can be applied to the profiled mold surface, and as the molten resin (or molten blend of resin and zeolite) is injected into the cavity of the mold, it forms around the projections creating indentations in the surface once it is ejected from the mold, and forcing the zeolite into those indentations. One suitable method of applying the zeolite to the mold surface is by electrostatic deposition, as deposition of zeolite particles on the mold substrate is enhanced by attractive electrostatic forces between particles and the surface. The injection molding process allows for a controlled, reproducible operation for producing the structure loaded with zeolite in the exposed surface region. The configuration, size (e.g., diameter and length) and spacing of the surface profile of the mold can be chosen based upon the desired exposed surface contour of the article. A combination of micro and macro channels or indentations can be formed, of dimensions suitable for promoting osseointegration and/or tissue integration when implanted into a host. Projections can be randomly oriented, or can be oriented in a uniform spaced array. Projections can be perpendicular to the mold surface, or can be oriented at an angle less than 90°, or both. Projections can have various shapes, including spikes or cones which taper axially to a sharp point, pyramidal, cylindrical, etc. Thus, the molding operation can be used to both form the article into the desired shape for the implant, and create the desired surface contour and introduction of large amounts of zeolite to the exposed surface region. A zeolite slurry can be introduced into the mold in the same manner as a suitable release agent is added to aid in release of the mold piece from the mold.

In a still further embodiment, the implant may be press molded in metal molds. A profiled or flat surfaced mold can be evenly coated with zeolite and naked resin or a resin/zeolite composite can be press molded, thereby coating the casting with a high level of imbedded zeolite in the exposed surface region.

In some embodiments, either natural zeolites or synthetic zeolites may be used to make the zeolites used in the embodiments disclosed herein. "Zeolite" is an aluminosilicate having a three-dimensional skeletal structure that is represented by the formula: $XM_{2/n} \cdot Al_2O_3 \cdot YsiO_2 \cdot ZH_2O$, wherein M represents an ion-exchangeable ion, generally a monovalent or divalent metal ion, n represents the atomic valency of the (metal) ion, X and Y represent coefficients of metal oxide and silica respectively, and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. A-type zeolites are particularly preferred, such as 4A zeolite having particle size ranges from 1 to 10 microns with a narrow distribution of about 4 microns.

Other ceramics and metal glasses are also envisaged instead of zeolite and are within the scope of the embodiments disclosed herein. For example, zirconium phosphate, bioglass or silver glass could be used.

In certain embodiments where the main body region of the article also is to include zeolite, fine zeolite powder may be incorporated into a powder of the thermoplastic polymer. For example, 4 micron powder of a 4A zeolite may be incorporated into molten PEEK powder that has a particle diameter of between about 10 to about 100 microns. In some embodiments, the incorporation of the zeolite into the polymer is carried out by thorough mixing the dry components at room temperature until the resulting composition is uniform by visual inspection. In some embodiments a drum roller can be used to carry out the mixing process.

The powder formulation may include the polymer, such as PEEK, and metal-loaded zeolite, such as silver zeolite. Other bioactive agents also may be included.

In certain embodiments, when metal cation is used, the metal cation is present at a level below the ion-exchange capacity in at least a portion of the zeolite particles. In some embodiments, the amount of zeolite mixed with the polymer may range from about 5 to 50 wt. %, more preferably about 10 to 20 wt. %. The amount of metal ions, if present, in the zeolite should be sufficient such that they are present in an antimicrobial effective amount when implanted into the body of a patient. For example, suitable amounts can range from about 0.1 to about 20 or 30% of the exposed zeolite (w/w %). These levels can be determined by complete extraction and determination of metal ion concentration in the extraction solution by atomic absorption. Preferably the ion-exchanged antimicrobial metal cations, if present, are present at a level less than the ion-exchange capacity of the ceramic particles. The amount of ammonium ions is preferably limited to from about 0.5 to about 15 wt. %, more preferably 1.5 to 5 wt. %. For applications where strength is not of the utmost importance the loading of zeolite can be taken as high as 50%. At such loadings the permeation of metal ions can permeate well below the surface layer due to interparticle contact, and much greater loadings of metal ions are possible.

In some embodiments, zeolite can be post-loaded with metal ions after it has been incorporated into the resin. Metal ion salt solutions, such as nitrates, acetates, benzoates, carbonates, oxides, etc., can be used to accomplish this. Addition of nitric acid to the infusion solution also may be advantageous in that it can etch the surface of the implant, providing additional surface area for ion exchange. That is, the zeolite may be charged with metal ions at a temperature between about 0 and 100° C., preferably about room temperature) from a metal ion source such as an aqueous metal ion solution, such as silver nitrate, copper nitrate and zinc nitrate, alone or in combination. Cooling to lower temperatures gives lower loading rates but higher stability. Loading at even higher temperatures can be carried out at a faster rate by maintaining the system under pressure, such as in a pressure cooker or autoclave. The content of the ions can be controlled by adjusting the concentration of each ion species (or salt) in the solution.

For example, the zeolite can be loaded with metal ions by bringing the composite material into contact with an aqueous mixed solution containing ammonium ions and antimicrobial and/or therapeutic metal ions such as silver, copper, zinc, strontium, etc. These materials will strongly inhibit attachment of microorganisms and can accelerate healing and reduce inflammation. By loading metal ions at these temperatures, deleterious oxidation of the metal ions that occurs at higher processing temperatures is reduced or eliminated. The most suitable temperatures at which the infusion can be carried out range from 5° C. to 75° C., but higher temperatures may also be used even above 100° C. if the reaction vessel is held under pressure. Higher temperatures will show increased infusion rates but lower temperatures may eventually produce more uniform and higher loadings. The pH of the infusion solution can range from about 2 to about 11 but is preferably from about 4 to about 7. Suitable sources of ammonium ions include ammonium nitrate, ammonium sulfate and ammonium acetate. Suitable sources of the metal ions include: a silver ion source such as silver nitrate, silver sulfate, silver perchlorate, silver acetate, diamine silver nitrate and diamine silver nitrate; a copper ion source such as copper(II) nitrate, copper sulfate, copper perchlorate, copper acetate, tetracyan copper potassium; a zinc ion source such as zinc(II) nitrate, zinc sulfate, zinc perchlorate, zinc acetate and zinc thiocyanate.

In some embodiments, the mechanical strength of the device may be reinforced by incorporating carbon fiber into the formulation. For example, milled carbon fiber may be added to the powder mixture of zeolite and polymer. The carbon fiber may also result in greater inter-layer adhesion and integrity of the device. The incorporation of fibers or other suitable reinforcing material(s) provides high wear resistance, a Young's modulus of 12 GPa (matching the modulus of cortical bone) and providing sufficient strength to permit its use in very thin implant designs which distribute the stress more efficiently to the bone. The amount of reinforcing material such as carbon fiber incorporated into the resin such as PEEK can be varied, such as to modify the Young's modulus and flexural strength. One suitable amount is 30 wt % carbon fiber.

In some embodiments, one or more biological agents can be added to the implant. Preferably they are incorporated after the implant has been cooled, since such agents typically do not tolerate high temperatures. Suitable biological agents include peptides, stem cells and growth factors such as bone morphogenetic proteins (BMPs). The BMPs are bioactive proteins that naturally occur in the human body and are regulated by various transcription and translation mechanisms. The BMPs belong to a family of growth factors that contribute to developmental processes such as pattern formation and tissue specification; in addition to inducing bone and cartilage formation, these proteins also regulate cell proliferation, migration, differentiation, and apoptosis in a number of tissues and organs. The BMPS have also been shown to promote wound healing and repair processes in adult tissues as well. A number of BMPs have been identified in humans and other animals including BMP-2, BMP-3 (osteogenin), BMP-3b (GDF-10), BMP-4 (BMP-2b), BMP-5, BMP-6, BMP-7 (osteogenic protein-1 or OP-1), BMP-8 (OP-2), BMP-8B (OP-3), BMP-9 (GDF-2), BMP-10, BMP-ii (GDF-11, BMP-12 (GDF-7), BMP-13 (GDF-6, CDMP-2), BMP-15 (GDF-9), BMP-16, GDF-1, GDF-3, GDF-5 (CDMP-1), and GDF-8 (myostatin). More recently, certain recombinant human BMPs have been approved by the Food and Drug Administration for limited clinical applications. For instance, INFUSE® is a commercially available product that delivers rhBMP-2 in an absorbable collagen sponge which may be placed into titanium spacers for the purpose of interbody fusion in the lumbar spine.

The resulting device may be introduced into the body surgically. Suitable hosts include mammals, including humans, canines, felines, livestock, primates, etc. The rate of release of antimicrobial metal ions, if present, is governed by the extent of loading of the polymer with zeolite and the extent to which the exposed zeolite is charged with metal ions. The electrolyte concentration in host blood and body fluids is relatively constant and will cause ion exchange with ions such as silver, copper and zinc, etc. from the surface of the implant, which deactivate or kill gram positive and gram negative organisms, including *E. coli* and *Staphylococcus aureus*. Effective antibacterial control (e.g., a six log reduction of microorganisms) is achieved even at low metal ion concentrations of 40 ppb.

Surface occupancy of zeolite can be determined indirectly by post loading the zeolite with a therapeutic metal ion, removing non absorbed metal by thorough rinsing and determining the amount which can be extracted into a 1% sodium nitrate solution by ICP OES. Comparison elution from a composite without the enhanced zeolite addition to the exposed surface region will give an indication of the extent of the surface enhancement of zeolite concentration.

| Component | Composition (w/w) % | Average particle size (Microns) |
|---|---|---|
| PEEK | 88 | 60 |
| 4A Zeolite | 12 | 4 |

Formulation Example 1

Formulation Example 2

| Component | Composition (w/w) % | Average particle size (Microns) |
|---|---|---|
| PEEK | 88 | 10 |
| 4A Zeolite | 12 | 4 |

Formulation Example 3

| Component | Composition (w/w) % | Average particle size (Microns) |
|---|---|---|
| PEEK | 73 | 10 |
| 4A Zeolite | 12 | 4 |
| Carbon Fiber | 15 | Milled strand |

Formulation Example 4

| Component | Composition (w/w) % | Average particle size (Microns) |
|---|---|---|
| PEEK | 73 | 10 |
| 4A Zeolite | 12 | 4 |
| Carbon Fiber | 15 | Milled strand |

Formulation Example 5

| Component | Composition (w/w) % | Average particle size (Microns) |
|---|---|---|
| PEEK | 43 | 10 |
| Sodium Chloride | 3 | 4 |
| 4A Zeolite | 12 | 4 |
| Carbon Fiber | 15 | Milled strand |

Example 1

Crystalline sodium chloride was mixed with Type 4A zeolite.

The mix ratio is not critical but in this Example, 7 grams of 4A Zeolite was mixed with 93 grams crystalline sodium chloride. The bottom of a metal container 60 mm diameter was covered with a layer of the salt/zeolite mixture. The container was placed in a furnace at 525° C. until it reached thermal equilibrium, which was about 20 minutes. The furnace may be flooded with inert gas to minimize the potential for oxidation.

A coupon of PEEK zeolite composite having 12% zeolite, 30 mm in diameter and 2 mm thick, was placed onto the surface of the heated salt. The system was rapidly placed back into the furnace and retained at temperature until the polymer softened.

The container was removed from the furnace and pressure applied to the top surface of the softened composite with a metal plunger 10 to 20 psi for 30 seconds. The system was allowed to cool and the coupon was removed and rinsed under running water, followed by immersion in distilled water until residual sodium chloride embedded in the surface was fully dissolved.

Example 2

A PEEK coupon, devoid of zeolite, 30 mm in diameter was heated for 90 seconds at about 525° C. in a furnace. A sheet of 80 mesh sandpaper was coated with 4A zeolite powder in an amount sufficient to cover the surface of the sandpaper. The softened PEEK coupon was removed from the furnace with tweezers and laid on the zeolite-coated sandpaper. Pressure of about 10 to 20 psi was applied to the softened PEEK for 30 seconds using a plunger.

On cooling the PEEK coupon was lifted from the surface and residual unattached zeolite was thoroughly rinsed from the surface. Visual observation indicated that a considerable amount of zeolite was bound to the surface.

Example 3

A coupon of a PEEK/zeolite composite containing 12% zeolite was evenly coated with a slurry of 4A zeolite in propanol and allowed to dry onto the surface. The coupon was heated to 525° C. in a furnace and pressed onto a sheet of 60 mesh sandpaper. The sample was rinsed as in Example 2. The surface of the polymer which was exposed to the sandpaper showed an indented profile as seen in FIG. 1.

Example 4

A continuous layer of zeolite slurry was applied to the surface of a PEEK coupon and allowed to air dry at room temperature to produce an adherent film of dried zeolite. Sodium chloride crystals were heated in the furnace as before and the zeolite-coated coupon was placed on the heated salt for 90 seconds and pressure applied as before for 30 seconds at 10 to 20 psi. The coupon was removed from the salt bed and allowed to cool and rinsed free of residual salt and residual unbonded zeolite with distilled water.

Example 5

A PEEK coupon, devoid of zeolite, 30 mm in diameter was heated in a furnace for 90 seconds at about 525° C. A sheet of 80 mesh sandpaper was coated with 4A zeolite powder.

The softened PEEK coupon was removed from the furnace with tweezers and laid on the zeolite-coated sandpaper. Pressure was applied to the softened PEEK using a plunger, about 10 to 20 psi for about 30 seconds.

On cooling, the PEEK coupon was lifted from the surface and residual unattached zeolite was thoroughly rinsed from the surface. Visual observation showed that a considerable amount of zeolite was bound to the surface.

Example 6

The inside surface of an injection molding mold engraved or etched with a suitable profile for application to the surface of a surgical implant to enhance osseointegration is used.

A spray slurry of 4A zeolite, in a suitable solvent such as water, is sprayed into the cavity of the mold in such as a way as to evenly coat the profiled surface of the mold, prior to injection of the shot of resin. The surface is allowed to dry and the resin is injected into the cavity of the mold. The melt presses hard into the profile of the mold and strongly bonds the zeolite particles to its surface.

During an injection molding run the mold is hot enough for the water to rapidly evaporate, leaving a uniform layer of zeolite on the mold surface.

While various aspects and embodiments have been disclosed herein, other aspects, embodiments, modifications and alterations will be apparent to those skilled in the art upon reading and understanding the preceding detailed description. The various aspects and embodiments disclosed herein are for purposes of illustration and are not intended to be limiting. It is intended that the present disclosure be construed as including all such aspects, embodiments, modifications and alterations insofar as they come within the scope of the appended claims or the equivalents thereof.

What is claimed is:

1. A method of making a medical implant having a main body region and an exposed surface region and comprising a polymer, the method comprising:
   a. heating the polymer to a molten state;
   b. contacting the polymer with a mixture of zeolite and an indentation-forming agent with the application of force to form indentations in said exposed surface region and drive said mixture into the formed indentations of the exposed surface region;
   c. cooling the polymer; and
   d. washing the resulting composite.

2. The method of claim 1, wherein said polymer is polyetheretherketone (PEEK).

3. A method of making a medical implant having a main body region and an exposed surface region and comprising a polymer, the method comprising:
   a. heating the polymer to a molten state;
   b. contacting the polymer with an indentation-forming member and zeolite to form indentations in said exposed surface region and drive the zeolite into the indentations in the exposed surface region; and
   c. cooling the resulting composite structure.

4. The method of claim 3, wherein said polymer is PEEK.

5. The method of claim 3, wherein said indentation-forming member comprises sandpaper.

6. A method of making a medical implant having a main body region and an exposed surface region and comprising a polymer, the method comprising:
   a. injecting the polymer into the cavity of a mold at elevated temperature sufficient to melt the resin, the mold comprising a surface having a plurality of projections and a coating of zeolite;
   b. causing the melted polymer to contact said projections and driving the zeolite into the resin; and
   c. removing the resulting article from the mold and cooling it.

* * * * *